United States Patent [19]

Elias et al.

[11] Patent Number: 4,935,555
[45] Date of Patent: Jun. 19, 1990

[54] PURIFICATION OF NEOPENTYL GLYCOL

[76] Inventors: Carole L. Elias, 240 Rampart Blvd., New Kensington, Pa. 15068; Marvin C. Fields, 316 Sunset Dr., Pittsburgh, Pa. 15235

[21] Appl. No.: 276,002
[22] Filed: Nov. 25, 1988
[51] Int. Cl.$^5$ ............... C07C 29/80; C07C 29/86; C07C 31/20
[52] U.S. Cl. ........................ 568/854; 568/853
[58] Field of Search ............ 568/854, 916, 921

[56] References Cited

U.S. PATENT DOCUMENTS

| | | | |
|---|---|---|---|
| 2,895,996 | 7/1959 | Wright, Jr. et al. | 260/637 |
| 2,930,818 | 3/1960 | Wüst | 260/637 |
| 3,037,060 | 5/1962 | Dege | 260/637 |
| 3,379,624 | 4/1968 | Lindkvist | 203/77 |
| 3,808,280 | 4/1974 | Merger et al. | 260/635 A |
| 3,920,760 | 11/1975 | Heinz | 260/635 A |
| 3,939,216 | 2/1976 | Wright | 568/853 |
| 3,975,450 | 8/1976 | Palmer et al. | 260/635 P |
| 4,021,496 | 5/1977 | Wright | 260/637 P |
| 4,038,329 | 7/1977 | Palmer et al. | 260/637 P |
| 4,250,337 | 2/1981 | zur Hausen et al. | 568/853 |
| 4,655,879 | 4/1987 | Brockmann et al. | 568/854 |

OTHER PUBLICATIONS

Pfaudler's "Wiped Film Evaporator" Sales Bulletin SB 39-100-1, pp. 1-8, 1984.

Primary Examiner—J. E. Evans
Attorney, Agent, or Firm—William L. Krayer

[57] ABSTRACT

In a process for the production of neopentyl glycol by hydrogenation of the aldol product of formaldehyde and isobutyraldehyde, an improvement comprises the wiped-film evaporator treatment of a saponified NPG-containing mixture. The process results in a very pure product and also eliminates the need for the addition of steam to the crude NPG, thus saving the cost of energy for removing the water from the NPG.

A further yield improvement is achieved by extracting NPG from the caustic residue with isobutyraldehyde and water. The isobutyraldehyde selectively recovers the NPG while the water selectively removes the caustic. The isobutyraldehyde and NPG are then conveniently recycled to the aldol reaction zone.

9 Claims, 1 Drawing Sheet

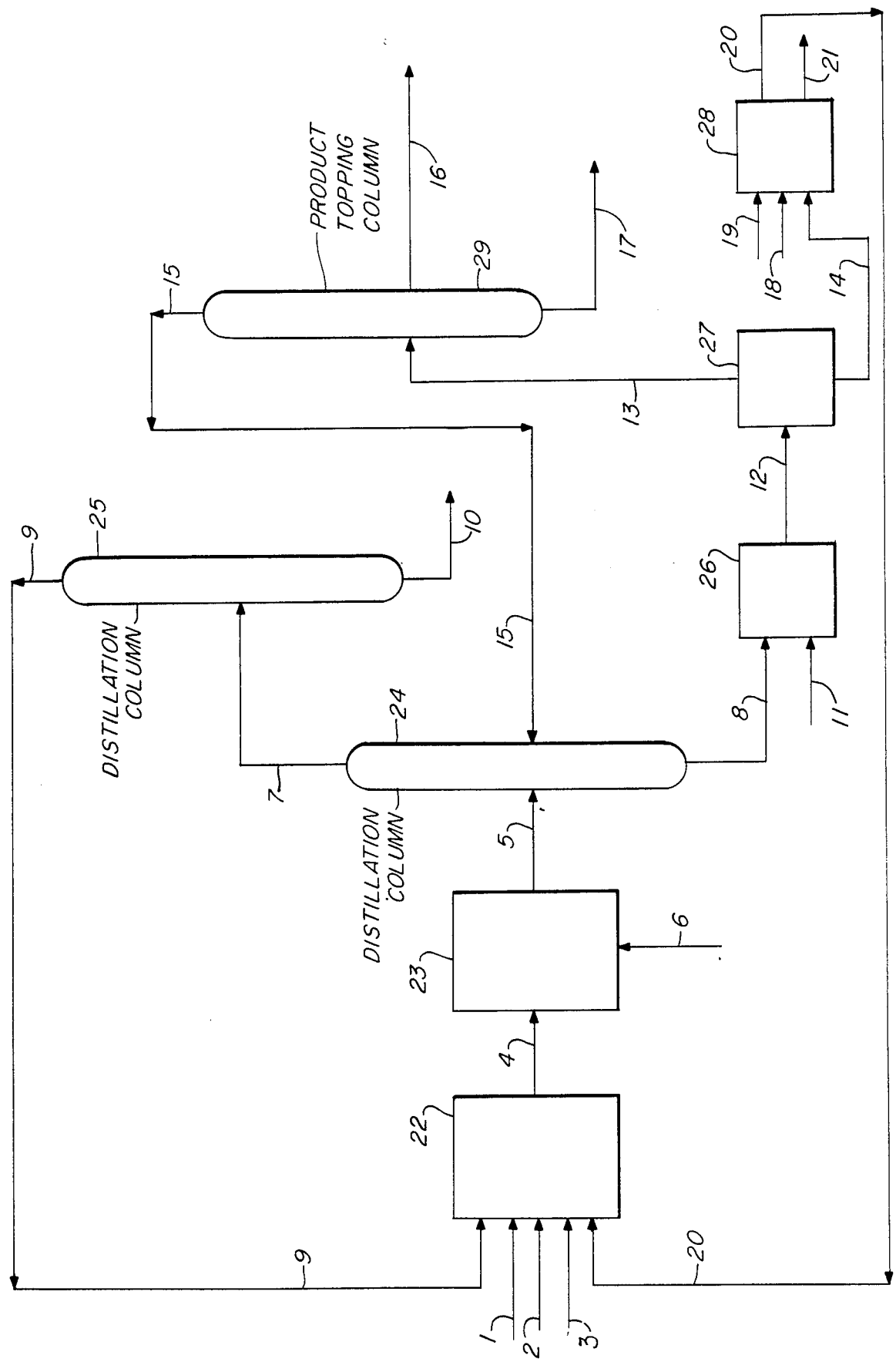

PURIFICATION OF NEOPENTYL GLYCOL

TECHNICAL FIELD

This invention relates to a significantly improved process for the purification of neopentyl glycol (NPG). Specifically, this invention comprises a process whereby high-purity NPG may be recovered in a less energy-intensive manner than previously known.

BACKGROUND OF THE INVENTION

The production of crude neopentyl glycol (NPG) is accomplished by well-known technology wherein formaldehyde and isobutyraldehyde undergo the aldol reaction in the presence of a basic catalyst. The aldol product, hydroxypivaldehyde, is hydrogenated in a conventional manner to produce a crude NPG product. The crude NPG typically contains various impurities, mainly NPG-isobutyrate and the self-condensation product of hydroxypivaldehyde. The NPG-isobutyrate, which boils at a temperature very close to the boiling point of NPG, is impractical to remove by conventional distillation. The self-condensation product of hydroxypivaldehyde, although easy to separate from the NPG by conventional distillation, represents a yield loss. These impurities are readily removed by saponification with caustic, which recovers NPG from the impurities and at the same time renders the impurities non-volatile. However, it is well known that the caustic-containing mixture is unstable at elevated temperatures, actually resulting in a less pure product when the caustic-treated NPG is distilled away from the caustic in a conventional distillation. Until now, no simple method has existed whereby the NPG could be recovered from the caustic.

U.S. Pat. No. 2,895,996 to Wright and Hagemeyer teaches that the saponified crude NPG may be subjected to a steam sublimation, whereby the NPG is recovered in an aqueous stream. The steam sublimation is conducted under reduced pressure (2–500 mmHg) and minimum temperature (60°–150° C.) in order to avoid the caustic-catalyzed decomposition of the NPG. The water, which may comprise 60-93% of the NPG-containing overhead stream from the sublimator, must be removed from the NPG by distillation. This results in a very energy-intensive process. In addition, some NPG must remain in the residue from the steam sublimation, and this represents a yield loss.

U.S. Pat. No. 3,939,216 to Wright describes an isobutyraldehyde extraction process for use on the caustic residue resulting from the following process: The aldol is caustic-catalyzed and the caustic-containing aqueous phase is separated from the hydroxypivaldehyde (HPA)-containing organic phase. The organic phase is hydrogenated, saponified with caustic to remove impurities, and then subjected to a steam-sublimation step. The residue from the steam-sublimation step is combined with the aqueous phase from aldol, and then the NPG is extracted with isobutyraldehde. The patent specifically limits the extraction feed to the combined streams, rather than the caustic residue stream only.

U.S. Pat. No. 4,021,496 to Wright also refers to the caustic-catalyzed aldol, wherein the caustic-containing aqueous stream is decanted from aldol and combined with the caustic residue from the steam-sublimation step. It claims an isobutyraldehyde (ibal) extraction of NPG from an "aqueous NPG-containing" stream and that the ibal can be used subsequently in aldol.

U.S. Pat. No. 4,038,329 to Palmer teaches a method for the purification of NPG made in the presence of an alkaline catalyst, whereby the NPG is extracted with a solvent such as isobutanol from the crude reaction product and then distilled under atmospheric pressure. Here, sodium is present as the aldol catalyst rather than for saponification of esters. The extraction is performed on the bulk of the NPG (i.e., prior to any distillation or evaporation), and accordingly some sodium is contained in the NPG and would be present in the subsequent atmospheric distillation.

DISCLOSURE OF INVENTION

Our specific improvement to the NPG purification process comprises performing the separation of the NPG from the caustic by evaporating the NPG in a wiped-film evaporator, such that no steam need be added to the NPG.

It is surprising that the NPG can be directly evaporated away from the caustic, without any decomposition occurring. It is well known that a conventional distillation of the saponified crude NPG results in a very impure product. Moreover, the previous art utilized steam to sublimate the NPG away from the caustic. We have found that a more efficient and simple method is to evaporate the NPG directly; by our process the exposure time to the heat is so short that no decomposition occurs.

It has been discovered that NPG can be directly evaporated away from a caustic residue at a pressure of about 10mm to about 100 mmHg, preferably about 80–100mmHg, and a jacket temperature of about 130° C. to about 180° C., preferably about 150° C. to about 180° C., in a wiped-film evaporator.

The amount of caustic which is used in the saponification step prior to the wiped-film evaporator depends on the level of impurities in the crude NPG. The crude NPG composition may contain up to about 10% by weight of impurities and more typically less than about 2% by weight. An excess of up to 25% over the stoichiometric amount of NaOH (compared to the impurities) is used to ensure total conversion of the impurities. It is desirable to minimize the amount of caustic used for economic reasons; however, greater or lesser amounts of caustic are operable and within the concept of the invention.

It has also been discovered that the small amount of NPG which remains with the caustic residue after the wiped-film evaporation step may be easily recovered by an extraction step utilizing isobutyraldehyde and water. The NPG may be extracted from the caustic residue of the wiped-film evaporator by adding to it about 0.5 to about 5 parts isobutyraldehyde and about 0.5 to about 3 parts water per part of caustic residue. The use of isobutyraldehyde is advantageous as it is a reactant used in the production of the intermediate hydroxypivaldehyde, which is hydrogenated to give NPG. Thus, the isobutyraldehyde, which selectively extracts the NPG from the caustic, may be conveniently recycled to the aldol feed. Since small amounts of NPG are present in aldol in any case, the NPG recycle is not deleterious to the reaction. The addition of water to the extraction results in the selective removal of the caustic, and has the additional benefit of yielding a flowable waste stream which may be easily handled. The extraction process is highly selective, with a high recovery of NPG, excellent removal of the caustic, and very low losses of isobutyraldehyde.

The resultant overall process produces a high-purity NPG in extremely high yields and does so in an energy-efficient and integrated manner.

BRIEF DESCRIPTION OF THE DRAWING

A preferred system for the process is shown more or less diagrammatically in the accompanying drawing. Formaldehyde is fed via line 1, isobutyraldehyde is fed via line 2, make-up catalyst triethylamine is fed via line 3, recycle catalyst triethylamine is fed via line 9, and recycle NPG is fed via line 20 to the aldol reactor 22 operated at 50° C. The aldol product is fed via line 4 to the hydrogenation reactor 23 where hydrogen is added via line 6. The hydrogenated product is fed via line 5 to a distillation column 24, where the light materials, including the catalyst, are removed overhead via line 7. The catalyst from line 7 is fed to distillation column 25, where the triethylamine is recovered for recycle to aldol reactor 22 via line 9. A waste stream leaves via line 10. The crude NPG leaves column 24 via line 8, where it is fed to stirred tank 26 to be treated with caustic fed through line 11. The caustic-treated NPG is fed to wiped-film evaporator 27 where the NPG is evaporated overhead via line 13. The NPG is fed to a topping column 29 where any lights are removed by line 15 and an optional heavies purge is taken via line 17, if needed. The NPG product leaves column 29 via line 16. The flowable caustic residue leaves the evaporator 27 via line 14, where it is fed to a decanter 28 and is contacted with isobutyraldehyde via line 18 and a small amount of water via line 19, whereby the isobutyraldehyde preferentially extracts the NPG from the residue and the caustic material leaves with the aqueous stream via line 21. The NPG is recycled back to the aldol reactor 22 via line 20.

COMPARATIVE EXAMPLE 1

About 681 g of crude NPG was saponified with 30 g of caustic. This material was then charged to a batch distillation column which was operated at a pressure of 70–75 mmHg and a final pot temperature of 169° C. The resultant gas chromatograph analyses obtained were as follows (caustic-free basis):

|  | Un-treated Feed | Caustic-treated Feed | First Cut | Second Cut | Pot Residue |
| --- | --- | --- | --- | --- | --- |
| Lights | 1.3% | 0% | 11.9% | 47.3% | 6.4% |
| NPG | 83.9% | 95.9% | 85.4% | 48.9% | 71.6% |
| NPG-formates | 0.8% | 0.1% | 0.4% | 0.4% | 0% |
| NPG-isobutyrate | 1.3% | 0.5% | 2.0% | 3.1% | 18.2% |
| HPA-ester | 12.4% | 3.5% | 0% | 0% | 0.5% |
| Heavies | 0.2% | 0% | 0% | 0% | 2.2% |

About 1000 g of crude NPG was treated with 25 g of caustic. The material was then fed to a wiped-film evaporator where the NPG was taken overhead away from the caustic residue at a pressure of 98 mmHG and a temperature of 160° C. The residue from the evaporator was a flowable solution and was continously removed. Analysis of the feed and products (caustic-free basis) is shown:

|  | Untreated Feed | Caustic-treated Feed | Distillate | Residue |
| --- | --- | --- | --- | --- |
| Lights | 1.1% | 0% | 0.1% | 0.3% |
| NPG | 92.3% | 99.5% | 99.6% | 99.4% |
| NPG-formates | 1.0% | 0.1% | 0% | 0.1% |
| NPG-isobutyrate | 1.1% | 0% | 0% | 0% |
| HPA-ester | 4.3% | 0% | 0.1% | 0% |
| Heavies | 0.2% | 0.3% | 0.3% | 0.2% |
| Sodium |  | .024% | <4 ppm |  |

Thus, it can be seen that the low residence time of the evaporator allowed the treated NPG to be evaporated at a relatively high temperature with no decomposition occurring. Although the feeds to the two treatments were different in purity, with a much purer feed being used in Example 2, it is apparent that significant product degradation occurred in the first example. Such product degradation is attributed to the long residence times inherent in conventional distillation. U.S. Pat. No. 2,895,996 supports this conclusion, reporting that degradation occurs in the presence of caustic during conventional distillation.

As is known in the art, a wiped film evaporator does not merely maintain a thin film on the evaporator surface by maintaining a fixed clearance, but agitates a film by remaining in direct contact with the product on the heated surface, i.e. by "trying" to contact the heat exchange surface directly. A wiped film is thus not only thinner than a simple "thin film" but implies a significant degree of agitation, a very thin film, and a very short residence time; in combination with a vacuum, the wiped film evaporator is known for its ability to vaporize heat-sensitive materials before they decompose on the heated surface. Wiped film evaporations may be compared in terms of pounds per hour of distillate treated per square foot of surface—however, even this will of course vary with the particular material treated. Any of the commercially available wiped film evaporators will be suitable for our purposes; the volume limits if throughput are determined by the equipment itself but typically will not operate properly if a wiped film as described above is not maintained.

EXAMPLE 3

10 g of caustic residue was obtained in a process similar to that of Example 2. To the residue was added 30 g of water and 35 g of isobutyraldehyde. The material was stirred until the residue dissolved, and after a time the two phases were separated and analyzed as shown:

|  | Aqueous Phase | Organic Phase |
| --- | --- | --- |
| Water | 89.98% | — |
| IBAL | 5.27% | 82.15% |
| NPG | 4.70% | 16.98% |
| Total Wt. | 37.51 g | 41.11 g |
| Sodium | 2750 ppm | 11 ppm |

In this manner, 79% of the NPG in the caustic residue was recovered by this step, with almost all of the sodium removed in the aqueous phase.

Thus our process includes a method of purifying neopentyl glycol obtained from the aldol reaction of formaldehyde and isobutyraldehyde comprising treating an impure NPG containing up to about 10% by weight impurities with an amount of NaOH effective to saponify said impurities, separating NPG from the caustic-treated NPG by processing it in a wiped-film evaporator, further treating the caustic-containing remainder of the impure NPG by adding thereto an amount of isobutyraldehyde effective to extract NPG therefrom, and recycling said NPG to the aldol reaction.

We claim:

1. In a method of making neopentyl glycol wherein formaldehyde and isobutyraldehyde are reacted and the aldol product thereof is hydrogenated to make a crude neopentyl glycol containing impurities, the improvement wherein impurities are removed from said crude neopentyl glycol comprising adding to said crude neopentyl glycol containing impurities an amount of sodium hydroxide effective to saponify impurities in said crude neopentyl glycol, passing said crude neopentyl glycol containing saponified impurities into a wiped-film evaporator, and evaporating at least a portion of said crude neopentyl glycol containing saponified impurities in said wiped-film evaporator at a temperature from about 130° C. to about 180° C. and a pressure of about 10 mm Hg to about 100 mm Hg.

2. Method of claim 1 wherein the wiped-film evaporator is operated at about 150° C to about 180° C.

3. Method of claim 1 wherein the wiped-film evaporator is operated at about 80 mmHg to about 100 mmHg.

4. Method of claim 1 including the additional step of extracting residual neopentyl glycol from the wiped-film evaporator by adding to the remainder of said crude neopentyl glycol after evaporating in said wiped-film evaporator an amount of isobutyraldehyde effective to extract neopentyl glycol from said remainder.

5. Method of claim 4 wherein an amount of water effective to separate caustic from said caustic-containing remainder is also added thereto.

6. Method of claim 4 wherein the isobutyraldehyde is added in an amount from about 0.5 to about 5 parts by weight per part of caustic-containing remainder.

7. Method of claim 5 wherein the amount of water added is about 0.5 to about 3 parts by weight per part of caustic-containing remainder.

8. Method of claim 4 wherein the impure NPG is obtained in an aldol reaction of formaldehyde and isobutyraldehyde and the NPG extracted from the wiped-film evaporator residue is recycled with the isobutyraldehyde therefrom to the aldol reaction.

9. Method of purifying neopentyl glycol comprising treating an impure neopentyl glycol with an amount of NaOH effective to saponify impurities therein, separating neopentyl glycol from the caustic-containing impure neopentyl glycol by evaporating said caustic-treated neopentyl glycol in a wiped film evaporator at a temperature from about 130° C. to about 180° C., at a pressure from about 10 mmHg to about 100 mm Hg, thereby also producing a caustic-containing remainder, extracting residual neopentyl glycol from the wiped film evaporator by adding to said caustic-containing remainder therein an amount of isobutyraldehyde effective to extract neopentyl glycol from said remainder and about 0.5 to about 3 parts by weight of water per part of caustic-containing remainder to separate caustic from said caustic-containing remainder.

* * * * *

UNITED STATES PATENT AND TRADEMARK OFFICE
CERTIFICATE OF CORRECTION

PATENT NO. : 4,935,555

DATED : June 19, 1990

INVENTOR(S) : Carole L. Elias and Marvin C. Fields

It is certified that error appears in the above-identified patent and that said Letters Patent is hereby corrected as shown below:

Column 3, line 60, insert before the paragraph the following heading -- EXAMPLE 2 --.

Signed and Sealed this

Seventeenth Day of September, 1991

Attest:

HARRY F. MANBECK, JR.

Attesting Officer

Commissioner of Patents and Trademarks